(12) United States Patent
Alexandre

(10) Patent No.: US 8,784,371 B2
(45) Date of Patent: Jul. 22, 2014

(54) NEEDLELESS INJECTION DEVICE EQUIPPED WITH A PROTECTED RESERVOIR

(75) Inventor: Patrick Alexandre, Gray (FR)

(73) Assignee: CROSSJECT (FR)

( * ) Notice: Subject to any disclaimer, the term of this patent is extended or adjusted under 35 U.S.C. 154(b) by 519 days.

(21) Appl. No.: 12/441,944

(22) PCT Filed: Aug. 31, 2007

(86) PCT No.: PCT/FR2007/001417
§ 371 (c)(1),
(2), (4) Date: Mar. 19, 2009

(87) PCT Pub. No.: WO2008/034960
PCT Pub. Date: Mar. 27, 2008

(65) Prior Publication Data
US 2010/0076375 A1    Mar. 25, 2010

(30) Foreign Application Priority Data
Sep. 19, 2006   (FR) ..................... 06 08166

(51) Int. Cl.
| | |
|---|---|
| *A61M 5/30* | (2006.01) |
| *A61M 37/00* | (2006.01) |
| *A61M 5/31* | (2006.01) |
| *A61M 5/28* | (2006.01) |
| *A61M 5/20* | (2006.01) |

(52) U.S. Cl.
CPC ......... *A61M 5/30* (2013.01); *A61M 2005/3132* (2013.01); *A61M 2005/287* (2013.01); *A61M 5/2046* (2013.01)
USPC ........................................ 604/69; 604/143

(58) Field of Classification Search
USPC ............................... 604/68–72, 140–148, 191
See application file for complete search history.

(56) References Cited

U.S. PATENT DOCUMENTS

| | | | | |
|---|---|---|---|---|
| 3,451,796 | A | * | 6/1969 | Mochel ............................. 65/31 |
| 3,464,414 | A | * | 9/1969 | Sponnoble .................... 206/221 |
| 6,264,629 | B1 | * | 7/2001 | Landau ........................... 604/68 |
| 2006/0189927 | A1 | * | 8/2006 | Alexandre et al. .............. 604/72 |

FOREIGN PATENT DOCUMENTS

| | | |
|---|---|---|
| FR | 2 853 836 | 10/2004 |
| FR | 2 853 837 | 10/2004 |
| FR | 2853837 A1 * | 10/2004 |
| FR | 2 865 407 | 7/2005 |
| FR | 2865407 A1 * | 7/2005 |
| WO | 01/97884 | 12/2001 |

OTHER PUBLICATIONS

International Search Report; PCT/FR2007/001417; Feb. 18, 2008.

* cited by examiner

*Primary Examiner* — Quynh-Nhu H Vu
*Assistant Examiner* — Jenna Zhang
(74) *Attorney, Agent, or Firm* — Cantor Colburn LLP

(57) ABSTRACT

Needleless injection device (1) comprising a gas generator (2), a reservoir (5) in the form of a glass tube (6) closed by an upstream stopper (7) and a downstream stopper (8) between which a liquid active principle (9) is accommodated, and an injection nozzle (15) equipped with a receptacle (19) and with at least one peripheral injection conduit (20), said tube (6) having, at one of its ends, a flange (4) via which it is in contact with said nozzle (15). The main feature of this needleless injection device (1) is that the tube (6) has a cylindrical inner channel with an upstream part (21) which is continued by a downstream part (22) of smaller diameter, said downstream part (22) being surrounded by said flange (4) and opening into the receptacle (19).

10 Claims, 1 Drawing Sheet

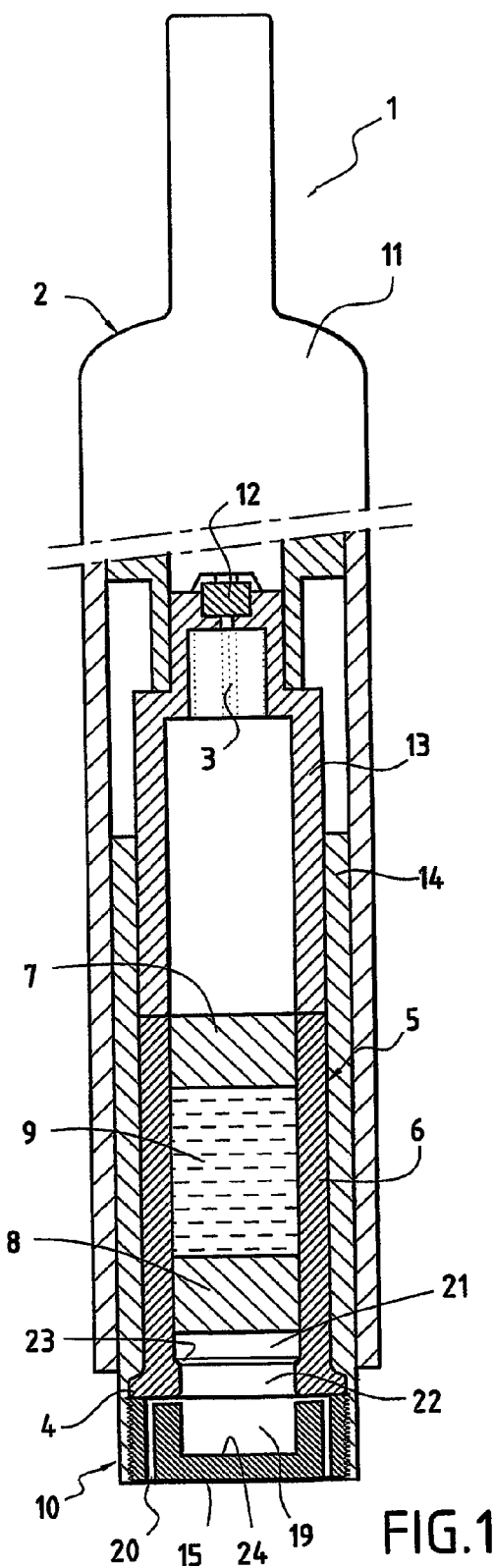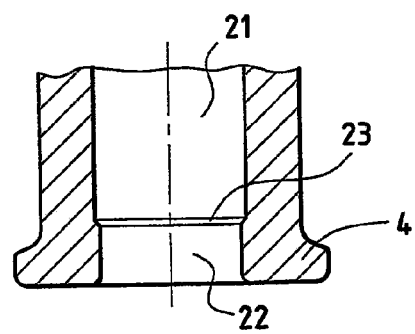
FIG.1
FIG.2

NEEDLELESS INJECTION DEVICE EQUIPPED WITH A PROTECTED RESERVOIR

BACKGROUND OF THE INVENTION

The technical field of the invention is that of prefilled, disposable needleless injection devices, operating with an energy source such as, for example, a gas generator and used for intradermal, subcutaneous and intramuscular injections of liquid active principle for therapeutic use in human or veterinary medicine.

The active principle consists of a more or less viscous liquid, a liquid mix, or a gel. The active principle may also be a solid in solution in a solvent suitable for injection, or consist of a powdery solid suspended at a certain concentration in an appropriate liquid. The particle size of the active principle must therefore be compatible with the diameter of the ducts to avoid blocking them.

Needleless injection devices comprising a reservoir of active principle already exist in tube form equipped with a flange and have been the subject of patents. For example, the patent application FR 2 853 837 may be cited, which relates to a needleless injection device comprising an injection nozzle and a tube intended to receive an active principle to be injected, said tube being fixed to said nozzle with the help of connecting means. The main technical feature of this injection device is that the tube containing the liquid active principle comprises a flange that will fit into fixed connecting means on said nozzle for joining said tube to said nozzle in a solid and reliable manner. The flange has a purely mechanical function which is that of a fixing piece.

BRIEF SUMMARY OF THE INVENTION

The aim of the invention is to minimize or even eliminate the risks of damage to the tube containing the liquid active principle and to the downstream stopper in the specific "double stopper" configuration. Said configuration is characterized by the presence of a column of liquid delimited, on the one hand, by the side wall of the tube and, on the other hand, by an upstream stopper and a downstream stopper, between which the liquid active principle is housed. Under the effect of the gas generation, said column moves in the tube until the downstream stopper comes into contact with the base of a receptacle located in the nozzle so as to free the peripheral injection channels in order to expel said active principle. When the downstream stopper hits the base of said receptacle, it creates a shock wave that will propagate through to the tube and the intensity of which is at a maximum at the end of said tube which is in contact with the nozzle. In order to resist this shock wave and therefore to prevent the tube shattering, the thickness of said tube at said end has been increased by the combination of a flange and an internal narrowing of said tube. Said narrowing also enables the downstream stopper to be prestressed by deforming it so as to facilitate its penetration into the receptacle. In summary, the narrowing of the tube both increases the thickness of the tube so as to increase its resistance to a shock wave and deforms the downstream stopper so as to facilitate its passage into the receptacle. This is because in a "double stopper" configuration, the downstream stopper and the glass tube are the two most stressed elements during the operation of the needleless injection device.

In the description and the claims the term "length" corresponds to a dimension taken along the axis of rotation of the tube and the term "thickness" corresponds to a dimension taken along a radial axis of said tube. In addition, the terms "stopper" and "stopper-piston" are equivalent.

More specifically, the invention relates to a needleless injection device comprising a gas generator, a reservoir constituted by a glass tube blocked by an upstream stopper and a downstream stopper, between which a liquid active principle is housed, and an injection nozzle equipped with a receptacle and with at least one peripheral injection duct, said tube possessing, at one of its ends, a flange by means of which it is in contact with said nozzle. The main feature of this device is that the tube has an internal channel comprising an upstream part extended by a downstream part of smaller diameter, said downstream part being surrounded by said flange and opening into the receptacle.

In this way, the end of the tube, which is in contact with the nozzle and which represents the zone of said tube most stressed by the shock wave reflected by the base of the receptacle following the impact of the downstream stopper, has an increased thickness due, on the one hand, to the presence of the flange and, on the other hand, to the narrowing of said downstream part.

The stopper is advantageously made of a deformable material so that, under the effect of the gas, it moves into the narrowing of the tube by deforming, before penetrating into the receptacle.

The length of the downstream part of the tube is preferably greater than or equal to the length of the flange.

The internal channel advantageously has a convergent part separating the upstream part from the downstream part. Thus, the passage of the downstream stopper from the upstream part of the tube toward the smaller diameter downstream part takes place gradually, facilitating its deformation, in contrast to a straight shoulder which would have a projecting edge likely to damage said stopper when passing.

The ratio between the diameter of the downstream part and the diameter of the upstream part is preferably between 0.85 and 0.98. Said ratio is advantageously 0.95.

The ratio between the length of the downstream part of the internal channel and the length of the stopper is advantageously between 0.5 and 2.0, preferably between 0.6 and 1.2.

The ratio between the thickness of the tube at the upstream part and the thickness of the tube at the flange is advantageously less than 0.5.

The ratio between the length of the flange and the thickness of the tube at said flange is advantageously between 0.1 and 0.8, preferably between 0.15 and 0.25.

The downstream stopper is advantageously solid and cylindrical, having a smooth external side wall and having a plane circular face at each of its ends. In other words, the stopper has a smooth shape overall, without any roughness likely to be torn or cut off the moment said stopper passes into the narrowed part of the tube.

The glass tube is preferably treated to improve its strength by chemical toughening, for example using molten potassium salt baths, or by thermal toughening, the levels of compressive prestressing to be attained at the surface being a minimum of 100 MPa.

The glass tube and the downstream stopper are advantageously siliconized to improve, in particular, the sliding qualities of the downstream stopper in the narrowed part of the tube.

The gas generator is preferably a pyrotechnic gas generator having an ignition system and a pyrotechnic charge.

The needleless injection devices according to the invention have the advantage of possessing a high safety level to the extent that the technical features of said syringes prevent breakage of the glass tube and damage to, or even fragmentation of, the downstream stopper when passing into the narrowed part of said tube. Said devices also have the advantage of being more reliable by incorporating a simple operational mechanism providing a certain fluidity in the movement of the parts involved.

BRIEF DESCRIPTION OF THE DRAWINGS

In the following a detailed description of two preferred embodiments of the invention is provided with reference to FIGS. 1 and 2:

FIG. 1 is a partial view, in longitudinal axial section, of a needleless injection device according to the invention; and FIG. 2 is a view, in longitudinal axial section, of the narrowed part of the tube of a needleless injection device according to the invention.

DETAILED DESCRIPTION OF THE INVENTION

With reference to FIG. 1, a needleless injection device 1 according to the invention comprises a pyrotechnic gas generator 2 composed of an initiation system and a pyrotechnic charge 3, a reservoir 5 constituted by a glass tube 6 blocked by an upstream stopper-piston 7 and a downstream stopper-piston 8 between which the liquid active principle 9 is contained, and an injection device 10. The tube 6 is advantageously made of a type I borosilicate glass.

The initiation system involves a striker 11, not detailed in FIG. 1, and a primer 12. The striker 11, which is triggered by a push button, comprises a spring and a weight provided with a striker pin (not shown). The weight is blocked by at least one ball wedged between said weight and the push button, and said push button has a circular internal groove.

The pyrotechnic charge 3 opens into an approximately cylindrical hollow body 13 which is itself extended by the tube 6 of the reservoir 5, said tube 6 having the same internal diameter as that of the hollow body 13. The tube 6 is continuous with the hollow body 13 and in contact with it, these two parts 6 and 13 also having the same external diameter. The latter are therefore perfectly aligned with one another and are maintained in this configuration by a plastic envelope 14 exerting a slight compression on the hollow body 13 and on the tube 6 after assembly. The envelope 14 starts approximately half way along the hollow body 13 and extends beyond the glass tube 6 with a hollow cylindrical front part, the internal side wall of which is threaded. With reference to FIG. 2, the tube 6 therefore has an upstream end that is in contact with the hollow body 13 and a downstream end provided with an annular flange 4 surrounding said end and located in a distal position in relation to the center of said tube 6. The tube 6 has an internal cylindrical channel comprising an upstream part 21 extended by a downstream part 22 of smaller diameter, said downstream part being surrounded by said flange 4. The upstream part 21 opens into the downstream part 22 by means of a convergent part 23, the largest diameter of which corresponds to the diameter of said upstream part 21 and the smallest diameter of which corresponds to the diameter of said downstream part 22. The end of the tube 6 provided with the flange 4 has a plane annular surface.

A hollow cylindrical part 15 playing the role of an injection nozzle and having a thread on its external side surface is screwed into the threaded hollow cylindrical front part of the envelope 14. The hollow part 15 has four peripheral injection ducts 20, parallel to each other and passing through said hollow part 15 over its entire length. Said ducts 20 are uniformly distributed around the hollow part 15. Said hollow part 15 comprises a cylindrical receptacle in the form of a central hollowing having a flat base 24.

When the hollow part 15 is screwed into the front part of the envelope 14, each longitudinal duct 20 finds itself extended by a radial channel opening into the upper part of the receptacle 19, said radial channel being delimited by both said hollow part 15 and the end of the glass tube 6 provided with the flange 4. More precisely, the hollow part 15 is screwed into the front part until its external peripheral part comes to stop against the end of the tube 6 provided with the flange 4. As the receptacle 19 is delimited by an internal annular part the length of which is less than that of the external peripheral part, with said internal and external parts being separated from one another by the injection ducts 20, a space is formed between said internal annular part and the end of the tube, in an extension of each of the peripheral ducts 20 passing through the nozzle 15.

The operational mode of this preferred embodiment of the invention is effected as follows. The user positions the needleless injection device 1 so that its end comes to bear on the skin of the patient to be treated. Pressure on the push button allows it to be slid along the needleless injection device 1 until the groove arrives level with the ball that blocks the weight. By being disengaged into the groove, the ball releases the weight which, under the effect of the contracting spring, is propelled toward the primer 12, the striker pin in front. The primer 12, which is then initiated, causes ignition of the pyrotechnic charge 3. The gases emitted exert pressure on the upstream stopper-piston 7 and the column of liquid constituted by the upstream 7 and downstream 8 stopper-pistons and the liquid active principle 9 starts a movement in the reservoir 5. The downstream stopper-piston 8 then passes through the narrowed downstream part of the tube 6 by deforming, without become cut or fragmented, due to the convergent part 23 of said tube 6, before being housed in the receptacle 19. Under the effect of the pressure, said downstream stopper-piston 8 deforms by "crashing" at the base of the receptacle 19, then allowing the liquid active principle 9 and the four peripheral injection ducts 20 of the nozzle 15 to come into contact. Said liquid 9 is then expelled toward the skin of the patient to be treated and this injection lasts until the upstream stopper-piston 7 comes into contact with the downstream stopper-piston 8 in the receptacle 19.

The invention claimed is:

1. A needleless injection device comprising:
   a gas generator;
   a reservoir constituted by a glass tube blocked by an upstream stopper and a downstream stopper, between which a liquid active principle is housed, and
   an injection nozzle equipped with a receptacle and with at least one peripheral injection duct,
   wherein said glass tube possesses, at one end, a flange by means of which said glass tube is in contact with said injection nozzle, said flange being a region of larger diameter of said glass tube; and
   wherein said glass tube has an internal channel comprising an upstream part extended by a downstream part of smaller diameter, said downstream part being surrounded by said flange and opening into the receptacle.

2. The needleless injection device as claimed in claim 1, wherein the internal channel has a convergent part separating the upstream part from the downstream part.

3. The needleless injection device as claimed in claim 1, wherein a ratio between a diameter of the downstream part and a diameter of the upstream part is between 0.85 and 0.98.

4. The needleless injection device as claimed in claim 1, wherein a ratio between a length of the downstream part of the internal channel and a length of the downstream stopper is between 0.5 and 2.0.

5. The needleless injection device as claimed in claim 1, wherein a length of the downstream part is greater than or equal to a length of the flange.

6. The needleless injection device as claimed in claim 5, wherein a ratio between a thickness of the glass tube at the upstream part and a thickness of the glass tube at the flange is less than 0.5.

7. The needleless injection device as claimed in claim 5, wherein the ratio between the length of the flange and the thickness of the glass tube at said flange is between 0.1 and 0.8.

8. The needleless injection device as claimed in claim 1, wherein the downstream stopper is solid and cylindrical, having a smooth external side wall and having a plane circular face at both ends.

9. The needleless injection device as claimed in claim 1, wherein the glass tube is treated to improve strength by chemical toughening or by thermal toughening.

10. The needleless injection device as claimed in claim 1, wherein the glass tube and the downstream stopper are siliconized.

\* \* \* \* \*